US006637257B2

(12) United States Patent
Sparks

(10) Patent No.: US 6,637,257 B2
(45) Date of Patent: Oct. 28, 2003

(54) MICROMACHINED FLUID ANALYSIS DEVICE AND METHOD

(75) Inventor: Douglas Ray Sparks, Whitemore Lake, MI (US)

(73) Assignee: Integrated Sensing Systems, Ypsilanti, MI (US)

( * ) Notice: Subject to any disclaimer, the term of this patent is extended or adjusted under 35 U.S.C. 154(b) by 0 days.

(21) Appl. No.: 10/065,578

(22) Filed: Oct. 31, 2002

(65) Prior Publication Data

US 2003/0121313 A1 Jul. 3, 2003

Related U.S. Application Data

(60) Provisional application No. 60/343,875, filed on Jan. 2, 2002.

(51) Int. Cl.[7] .............................................. G01N 15/08
(52) U.S. Cl. ...................... 73/38; 73/61.63; 73/61.71; 422/68.1; 422/101; 422/255; 422/267; 436/12; 436/14; 436/15; 436/163; 436/177; 436/178
(58) Field of Search ...................... 73/38, 61.63, 61.71, 73/61.72; 422/68.1, 82.01, 82.02, 101, 255, 261, 267; 436/8, 12, 14, 15, 16, 163, 177, 178

(56) References Cited

U.S. PATENT DOCUMENTS 5,626,734 A * 5/1997 Docoslis et al. ............ 204/547
6,264,815 B1 * 7/2001 Pethig et al. ............... 204/547

OTHER PUBLICATIONS

Kittilsand, Gjermund, et al; *A Sub–micron Particle Filter in Sillicon*; Sensors and Actuators, A21–A23; 1990; pp. 904–907.

Van Rijn, Cees, et al; *Deflection and Maximum Load of Microfiltration Membrane Sieves Made With Silicon Micromachining*; Journal of Microelectromechanical Systems, vol. 6, No. 1; Mar. 1997; pp. 48–54.

Katsube, T., et al; *pH–Sensitive Sputtered Iridium Oxide Films*; Sensors and Actuators, 2; 1982; pp. 399–410.

Pasztor, K, et al; *Iridium Oxide–based Microelectochemical Transistors for pH Sensing*; Sensors and Actuators B, 12; 1993; pp. 225–230.

* cited by examiner

*Primary Examiner*—Daniel S. Larkin
(74) *Attorney, Agent, or Firm*—Gary M. Hartman; Domenica N. S. Hartman; Hartman and Hartman, P.C.

(57) ABSTRACT

A method and device for performing fluid analysis by separating cells and/or particles from a fluid, such as a biological, vehicular or industrial fluid. The device is a micromachined filtering device comprising a substrate with through-thickness vias having approximately equal diameters that prevent passage through the substrate of a first material while permitting passage through the substrate of other materials having diametrical dimensions less than the diameter of the vias. Electrodes are located on a surface of the substrate between vias so that as the first material collects at the surface of the substrate, the electrodes become electrically connected to produce an output signal in some proportion to the amount of the first material collected. The device can incorporate multiple micromachined substrates, yielding an analysis system that produces an electrical output for each of a number of properties or parameters.

46 Claims, 3 Drawing Sheets

MICROMACHINED FLUID ANALYSIS DEVICE AND METHOD

CROSS REFERENCE TO RELATED APPLICATIONS

This application claims the benefit of U.S. Provisional Application No. 60/343,875, filed Jan. 2, 2002.

BACKGROUND OF INVENTION

1. Field of the Invention

The present invention generally relates to fluid analysis methods and equipment.

More particularly, this invention relates to a fluid analysis device and method that utilize a micromachined filter to separate cells and/or particles from a fluid, such as a biological fluid, and means for sensing the material selectively separated from the fluid with the filter.

2. Description of the Related Art

Various fluids undergo some type of quantitative analysis to determine their composition and physical properties. Notable examples of such fluids include urine, blood, beverages, pharmaceutical mixtures, water, lubricating oils, fuels, and many industrial chemicals. With regard to urological analysis, a variety of parameters are typically measured during urology, including pH, specific gravity, and the amount of blood, leukocytes (white blood cells), glucose, protein, urobilinogen, bilirubin, ketones, nitrite, sodium, chlorine, potassium, magnesium, urea, uric acid, bicarbonate, sulfate, phosphate and calcium. The specific gravity of urine can be used as a screen to indicate renal and hepatic problems, with additional urinary tests being performed as necessary if a problem is indicated.

The specific gravity of urine has been measured by various methods, including ultrasonic and optical techniques as disclosed in U.S. Pat. Nos. 4,664,124 and 4,834,104, respectively. More recently, commonly-assigned U.S. patent application Ser. No. 09/468,628 to Tadigadapa et al. discloses a resonant mass flow and density sensor suitable for quantitative analysis of fluids. The sensor comprises a suspended tube that is vibrated at resonance. As fluid flows through the tube, the tube twists under the influence of the Coriolis effect. The degree to which the tube twists (deflects) when vibrated can be correlated to the mass flow rate of the fluid flowing through the tube, while the density of the fluid is proportional to the frequency of vibration. The tube is fabricated by micromachining, which as used herein denotes a technique for forming very small elements by bulk etching a substrate (e.g., a silicon wafer) or by surface thin-film etching, the latter of which generally involves depositing a thin film (e.g., polysilicon or metal) on a sacrificial layer (e.g., oxide layer) on a substrate surface and then selectively removing portions of the sacrificial layer to free the deposited thin film.

Various other parameters of interest in urological analysis have been measured using reagent test strips. However, there are drawbacks to the use of test strips, including the vulnerability to humidity, finger contamination, and erroneous results due to vitamin C intake prior to testing. Test strips also require a manual operation and the constant expense of replacement since they are consumed by the test.

Biological fluid filtration has also been utilized in the field of fluid analysis. For example, physical filtration of donated blood has been used for years to separate leukocytes from plasma. For urological applications, the concentration of leukocytes is often of interest, as their presence in urine can indicate a urinary tract infection from chronic catheter use as well as renal and hepatic problems. Leukocytes are larger (about twenty micrometers) than other blood or urine components, and so can be physically filtered. Micromachined filters, including silicon filters, capable of use in urological analysis have been proposed, as disclosed in U.S. Pat. Nos. 5,660,728 and 5,922,210.

While fluid analysis techniques and devices of the types described above have been successfully employed, there is a continuing effort to develop improved devices for performing fluid analysis. For example, the capability for continuous monitoring would be desirable, particularly in the form of remote monitoring of disabled catheterized patients. In addition, it would be desirable if components grouped into a single system could perform multiple analysis steps, such that an accurate diagnosis can be made with a single sample.

SUMMARY OF INVENTION

The present invention provides a method and device for performing fluid analysis utilizing a micromachined filter to separate cells and/or particles from a fluid, such as a biological fluid. The device has the additional capability of sensing the relative quantity of cells and/or particulate material selectively separated from the fluid with the filter. Multiple micromachined filters of this invention can be integrated into a single device that produces an electrical output for each of a number of urological parameters, providing a rapid and simplified interface capable of remote and continuous monitoring of a fluid.

According to a first aspect of the invention, the device is a micromachined filtering device comprising a substrate having a first surface, an oppositely-disposed second surface, and a thickness defined by and between the first and second surfaces. A plurality of vias extend through the thickness of the substrate, with the vias being spaced apart and having approximately equal diameters that prevent passage through the substrate of materials (e.g., cells and/or particles) having a diametrical dimension greater than the diameters of the vias, while permitting passage through the substrate of a fluid and any other materials present in the fluid and having a diametrical dimension less than the diameters of the vias. First and second electrodes are, located on the first surface of the substrate so that the materials too large to pass through the vias, and have therefore collected at the first surface of the substrate, will electrically connect the first and second electrodes to produce an output signal in proportion to the amount of the material collected.

As a result of the construction of the device, the present invention makes possible a method of quantitatively analyzing a fluid by flowing the fluid through the vias in the substrate, whereby the fluid and any cells and/or particles smaller than the vias are permitted to pass through the substrate, while cells and/or particles larger than the vias are prevented from passing through the substrate, such that the larger cells/particles collect at the first surface of the substrate. The amount of the collected cells/particles at the first surface of the substrate is indicated by the output signal obtained from the electrodes.

Fluid filtering in accordance with this invention may be preceded or followed by additional analysis, such as the measurement of specific density, pH, and various constituents detected with chemical sensors. In the case of urological analysis, such constituents include glucose, protein, urobilinogen, bilirubin, ketones, nitrite, pH, sodium, chlorine, potassium, magnesium, urea, uric acid, bicarbonate, sulfate, phosphate, and calcium. With the present invention, such analysis can be preformed on multiple substrates within a single device, yielding a single-system sensing and filtering system.

Other objects and advantages of this invention will be better appreciated from the, following detailed description.

DETAILED DESCRIPTION

Figure 1:
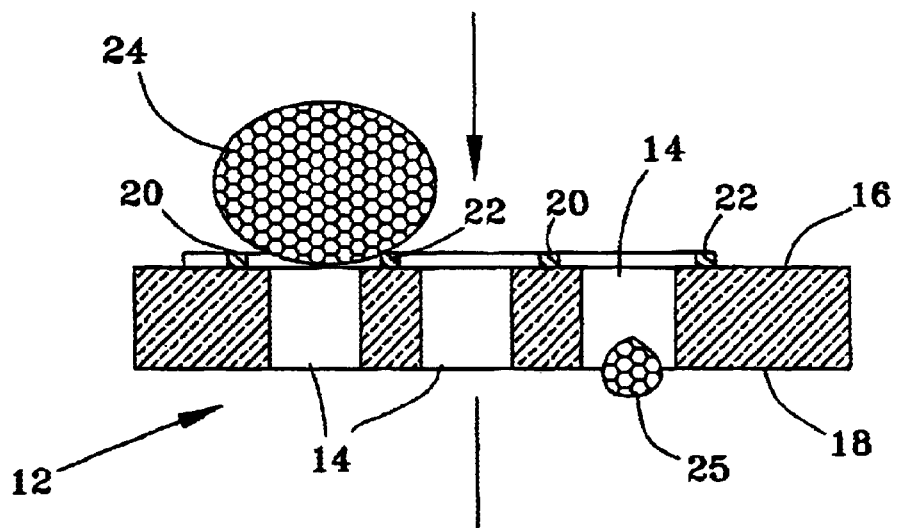
FIGS. 1 and 2 are cross-sectional and plan views, respectively, of a substrate of a micromachined filtering device in accordance with this invention.
Figure 2:
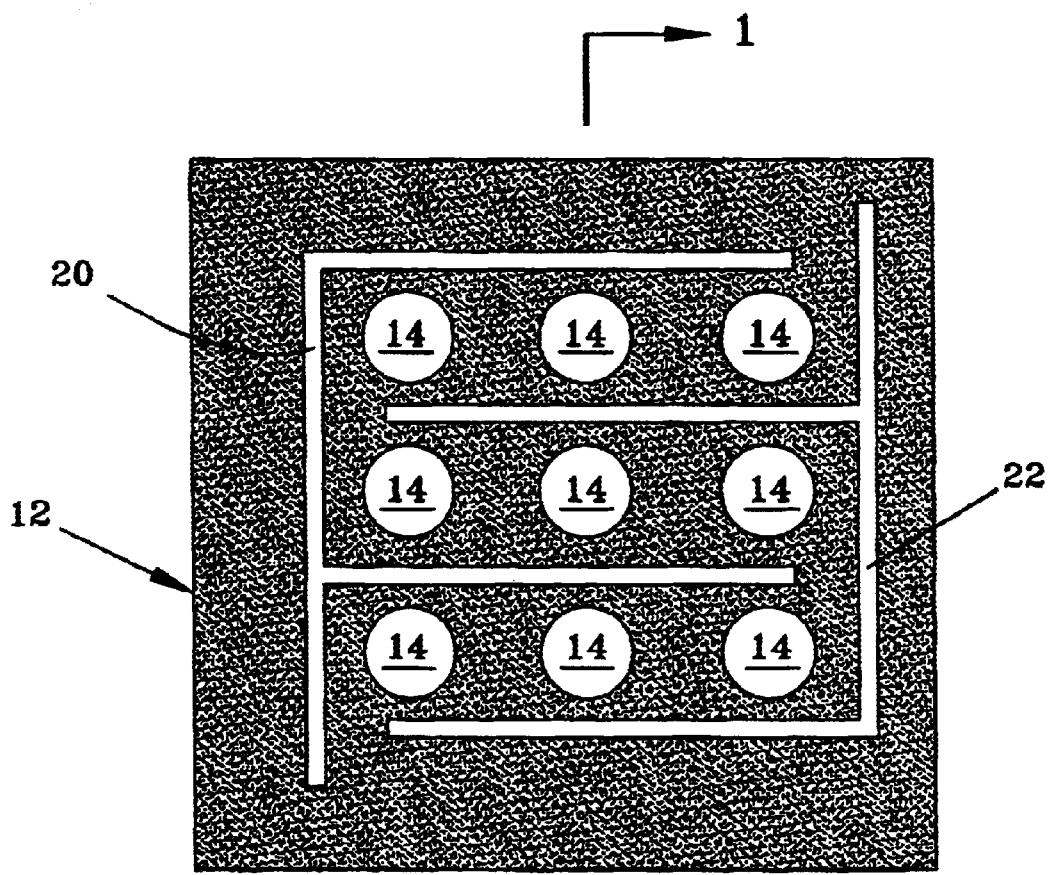
Figure 3:
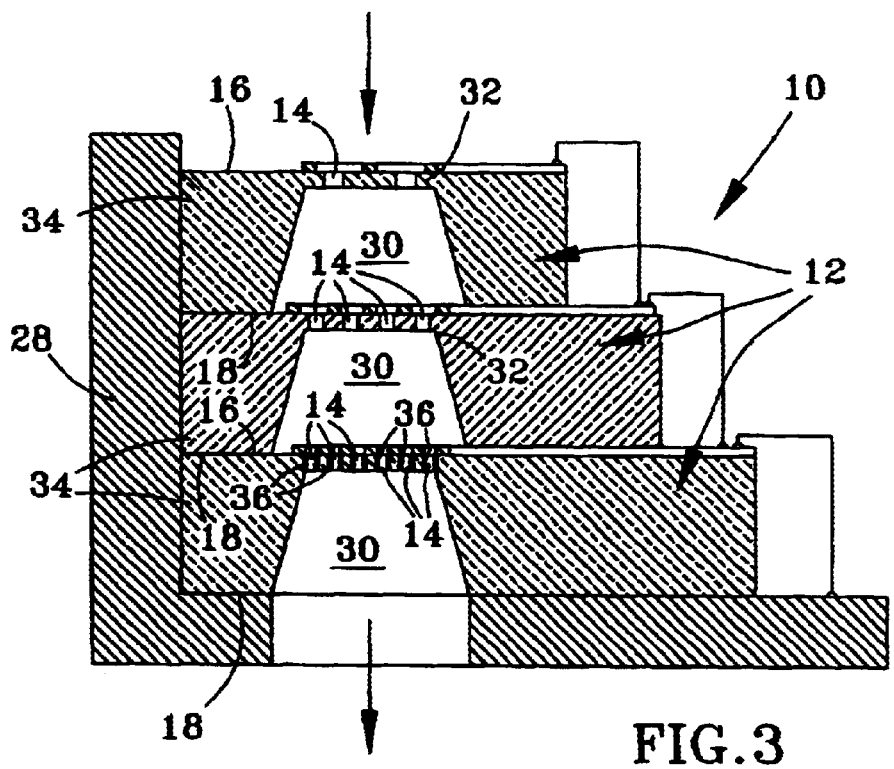
FIGS. 3 and 4 are cross-sectional views of micromachined filtering devices in accordance with two embodiments of the invention.
Figure 4:
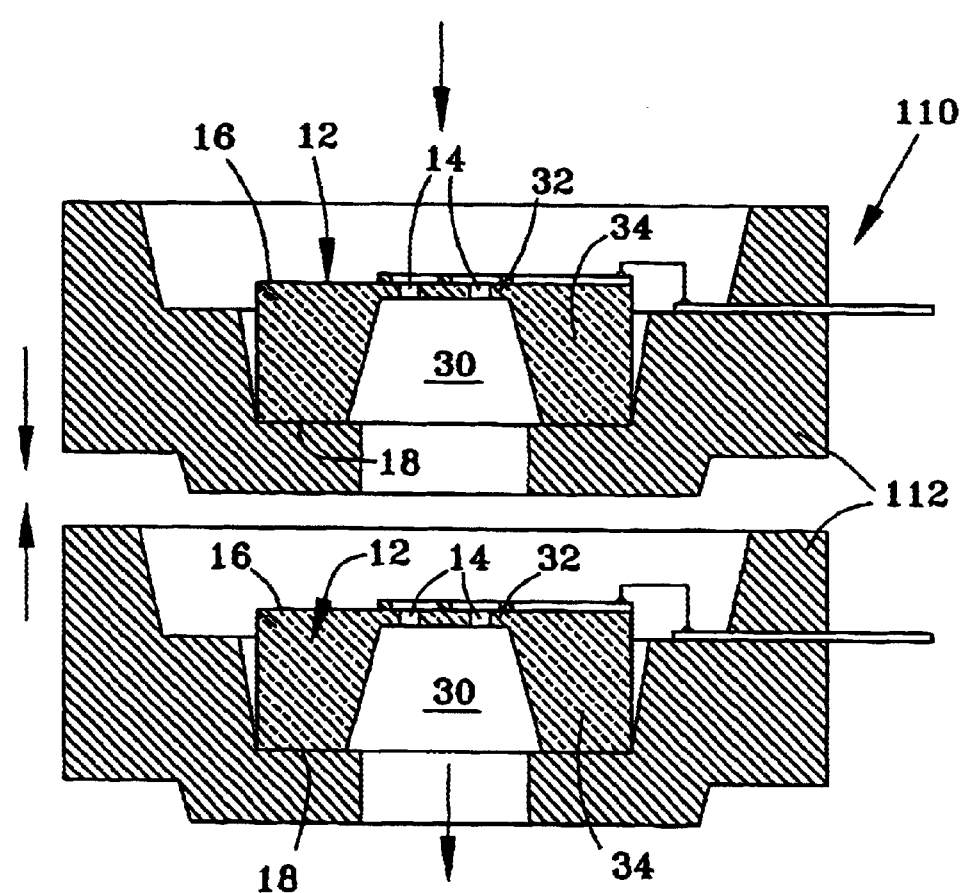

FIGS. 1 and 2 represent a substrate 12 for a micromachined filtering device in accordance with the invention, two embodiments of which are represented in FIGS. 3 and 4. The substrate 12 can be formed of silicon, such as silicon doped to be p-type. Alternatively, the substrate 12 can be formed of another semiconductor material, quartz, ceramic, metal, or a composite material. Vias 14 are micromachined in the substrate 12 to have approximately identical diameters, and to extend through the thickness of the substrate 12 between opposing surfaces of the substrate 12, referred to herein as upstream and downstream surfaces 16 and 18. The vias 14 are preferably etched through the substrate 12 using known semiconductor processing. For example, if the substrate 12 is formed of silicon, the vias 14 can be formed by masking either of the surfaces 16 or 18 of the substrate 12, followed by etching with a wet chemical anisotropic etchant, such as ethylenediamine pyrocatechol (EDP), or an alkali-type etchant, such as potassium hydroxide (KOH) and tetramethyl ammonium hydroxide (TMAH).

As seen in FIG. 2, the vias 14 are arranged in an array (rows and columns), with rows of the vias 14 being separated by interdigitized portions of two electrodes 20 and 22 on the upstream surface 16 of the substrate 12. The vias 14 are arranged and adapted to serve as passages through which a fluid, such as urine, blood, beverage, pharmaceutical mixture, water, oil, fuel, industrial chemical, etc., flows for the purpose of performing quantitative analysis of the fluid. More particularly, the vias 14 are sized to filter from the fluid any cells and/or particles 24 that exceed the diameter of the vias 14, while permitting the entraining fluid and smaller cells/particles 25 to pass through the substrate 12, as represented in FIG. 1. For example, if the fluid is urine, the cells/particles that may be filtered with the substrate 12 include blood, or selectively leukocytes and erythrocytes (red blood cells). As will be discussed below in reference to urological analysis that can be performed with the teachings of this invention, a variety of parameters can be measured with a device utilizing the substrate 12, including pH, specific gravity, and the amount of glucose, protein, urobilinogen, bilirubin, ketones, nitrite, sodium, chlorine, potassium, magnesium, urea, uric acid, bicarbonate, sulfate, phosphate, and calcium. Other fluids that can be processed with such a device include any that contain biological cells, spores, or particles from essentially any source.

In view of the above, the diameter of the vias 14 is chosen to prevent the passage through the substrate 12 of cells/particles of a particular size and larger, while permitting the entraining fluid and smaller cells/particles 25 to pass through the substrate 12. For example, leukocytes (diameter of about twenty micrometers) can be filtered with an array of vias 14 on the order of about fifteen to seventeen micrometers in diameters, while allowing water (95% of urine), electrolytes, protein, glucose, and erythrocytes to pass through. The monitoring of the presence of erythrocytes in urine is also desirable as being useful to detect cardiovascular, renal, and hepatic problems. For this purpose, erythrocytes (about eight micrometers in diameter) can be subsequently filtered with a second substrate 12 having appropriately-sized vias 14, e.g., having a size range of about three to seven micrometers. The quantity of cells filtered from the fluid is then determined by the electrical resistance or current flow that occurs between the electrodes 20 and 22 when a potential is applied across the electrodes 20 and 22. In particular, as the electrodes 20 and 22 become electrically connected by cells/particles that collect at the upstream surface 16 of the substrate 12, current flow between the electrodes 20 and 22 will progressively increase, and electrical resistance progressively decrease, to produce an output signal in some proportion to the amount of material collected at the upstream surface 16. Suitable materials for the electrodes 20 and 22 include platinum or iridium runners of a type known in the art for thick-film hybrid circuits. If the substrate 12 is formed of silicon or another conductive or semiconductive material, the upstream surface 16 on which the electrodes 20 and 22 are formed is preferably oxidized or otherwise provided with an electrically insulating layer prior to the deposition of the electrodes 20 and 22. In addition to the electrodes 20 and 22, a chemically-active material can be deposited on the upstream surface 16 in combination with the electrodes 20 and 22 to increase sensitivity. Such a material can be a biological material that attracts leukocytes through an immunological reaction.

As shown in FIGS. 3 and 4, multiple substrates 12 of the type shown in FIGS. 1 and 2 can be utilized in a single filtering device 10 or 110, so that incrementally, smaller cells/particles can be filtered from a fluid. In FIG. 3, three substrates 12 are bonded together and then packaged in a housing 28 as a single filtering device 10. The device 110 shown in FIG. 4 differs from that of FIG. 3 by individually packaging the substrates 12 in packages 112, which are then bonded or otherwise secured together. In both embodiments, the downstream surface 18 of each substrate 12 is shown as having been etched to form a recess 30 that defines a membrane 32 surrounded by a frame 34. In FIG. 3, the frames 34 of the substrates 12 are bonded directly together, e.g., anodically or with a screen-printed adhesive or glass frit, at the die or wafer bonding level.

In each of the embodiments of FIGS. 3 and 4, the uppermost substrate 12 is preferably micromachined to have vias 14 sized to filter relatively large cells or particles, e.g., leukocytes, while the middle and lowermost substrates 12 of FIG. 3 and the lowermost substrate 12 of FIG. 4 are micromachined to have vias 14 sized to filter relatively smaller cells or particles, e.g., erythrocytes. Alternatively or in addition, the lowermost substrates 12 of FIGS. 3 and 4 can be adapted to sense other parameters of the fluid which, depending on the fluid, may include pH or the amount of certain constituents in the fluid. For example, if the fluid is urine, the lowermost substrates 12 can be adapted to determine the amount of glucose, protein, urobilinogen, bilirubin, ketones, nitrite, sodium, chlorine, potassium, magnesium, urea, uric acid, bicarbonate, sulfate, phosphate, or calcium in the fluid. For this purpose, chemical sensors 36 are shown in FIG. 3 as being embedded in the walls of the vias 14. Alternatively or in addition, the sensors 36 could be located on the upstream surface 16 of the substrate 12, or in the walls of the recess 30 in the downstream surface 18 of the substrate 12. For urology, the chemical sensors 36 are preferably located downstream of substrates 12 used to filter leukocytes and erythrocytes, as represented in FIG. 3. As also represented in FIG. 3, the substrate 12 on which the chemical sensors 36 are provided can be placed directly in the fluid flow stream. Alternatively, the substrate 12 could be placed so as to be immersed in a relatively static pool of the fluid for longer exposure times. Any number of substrates 12 equipped with chemical sensors can be employed to increase the number of chemicals monitored. The chemical sensors 36 may be formed by a variety of materials, such as certain metal oxides and organic films known in the art to be sensitive to the parameters of interest, an example of which is pH-sensitive iridium oxide films. Other suitable chemical sensors and methods for forming such sensors in the substrate 12 are known to those skilled in the art, and therefore will not be discussed in any further detail here.

According to the invention, the devices 10 and 110 can be modified to sense the specific gravity of the fluid, such as by including the resonant mass flow and density sensor disclosed in commonly-assigned U.S. Pat. No. 6,477,901 to Tadigadapa et al., incorporated herein by reference. For this purpose, another substrate equipped with a suspended micromachined tube would be placed upstream of the uppermost substrate 12 of FIGS. 3 and 4. In accordance with Tadigadapa et al., the tube is fabricated to comprise a fluid inlet, a fluid outlet, and a freestanding portion therebetween, with the freestanding portion being spaced apart from a surface of the substrate. Means is provided for vibrating the freestanding portion of the tube, preferably at resonance, and for sensing movement of the freestanding portion relative to the substrate in a manner that permits the density of the fluid to be determined, from which specific gravity can be calculated by comparing the density of the fluid to the density of water. In urology, the specific gravity of urine obtained in this manner can then be utilized as a screen for renal and hepatic problems. With the present invention, additional quantitative analysis can be advantageously performed immediately downstream of the resonating tube with one or more of the micromachined filtering devices 10/110.

Figure 5:
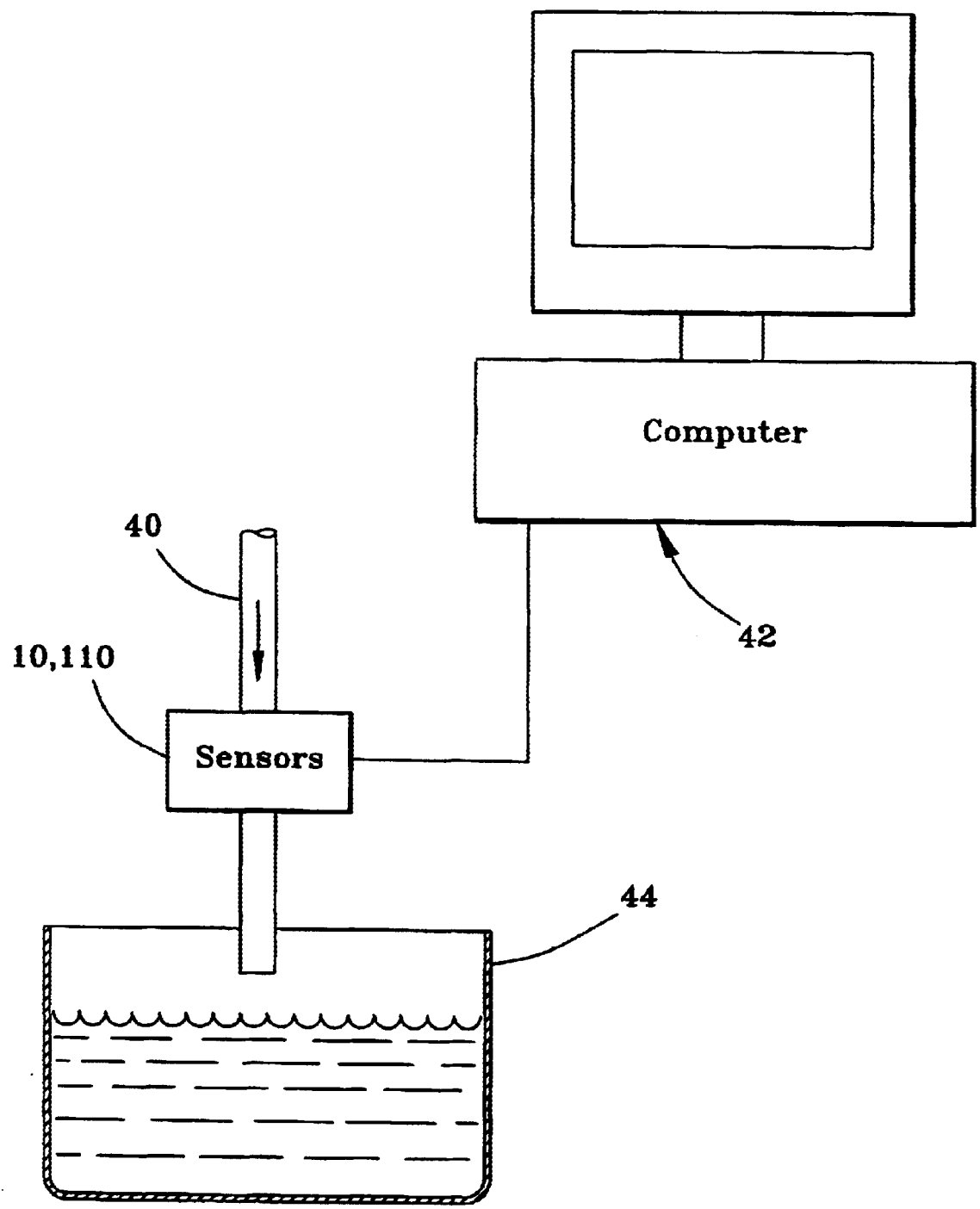
FIG. 5 represents a urological analysis system utilizing a micromachined filtering device of this invention.

In view of the above, the present invention enables a diagnosis to be obtained using a series of tests performed on a single sample with a single device. FIG. 5 represents such an analysis system, in which a catheter 40 attached to a patient delivers a bodily fluid, e.g., urine, to a filtering device 10/110 of this invention. In accordance with the above, the device 10/110 may include one or more substrates 12 for filtering urine, as well as one or more substrates 12 equipped with chemical sensors 36 (FIG. 3) and optionally an additional substrate for sensing density in accordance with Tadigadapa et al. The several output signals from the individual substrates 12 are relayed to a computer 42 for analysis, with the filtered urine being dispensed to a drain reservoir 44. While FIG. 5 shows the device 10/110 in series with the catheter 40 and reservoir 44, the device 10/110 could be placed in a passage branching off from the catheter 40 and parallel to a drain tube, with both the drain tube and an output tube from the device 10/110 dispensing urine to the reservoir 44. Other configurations are envisioned, including the sampling of fluid from a sample reservoir that accumulates fluid from the catheter 40, or sampling fluid directly from the reservoir 44.

In view of the above, the present invention provides the capability of measuring a wide variety of fluid properties and parameters, providing a physician with the ability to monitor and diagnose a variety of ailments, such as renal, hepatic, pancreatic, gastrointestinal, and cardiovascular problems via urology. The ability to fabricate the device 10/110 as a reusable device, miniaturized through the use of micromachining technology, is beneficial to both specialists (e.g., urologists) and general practitioners. The device 10/110 of this invention is particularly well suited to provide continuous monitoring of disabled, catheterized patients. By appropriately controlling fluid flow through the device 10/110, a manual or automatic back-flushing operation can be performed to remove cells/particles that have collected at the upstream surface 16 as the need requires. Otherwise, healthcare workers need only intervene if the output of the device 10/110 indicates that a medical concern exists, which can be relayed in the form of an alarm system triggered if abnormal cell or chemical levels exceed a predetermined limit over a given period of time or for the flow rate through the device 10/110. The electrical output signal(s) that can be produced by the device 10/110 also enables remote computer monitoring of urinary output to provide early indicators of ailments, which is especially important for diabetic and disabled patients and can greatly reduce the cost of long-term health care While the invention has been described in terms of certain embodiments, it is apparent that other forms could be adopted by one skilled in the art. Therefore, the scope of the invention is to be limited only by the following claims.

What is claimed is:

1. A micromachined filtering device comprising:
    a substrate having a first surface, an oppositely-disposed second surface, and a thickness defined by and between the first and second surfaces;
    a plurality of vias through the thickness of the substrate, the vias being spaced apart and having approximately equal diameters that permit passage through the substrate of material having a diametrical dimension less than the diameters of the vias and to prevent passage through the substrate of material having a diametrical dimension greater than the diameters of the vias; and
    first and second electrodes on the first surface of the substrate, the first and second electrodes being located on the first surface so that material that is too large to pass through the vias and therefore collects at the first surface of the substrate will electrically connect the first and second electrodes to produce an output signal in proportion to the amount of material collected at the first surface.

2. A micromachined filtering device according to claim 1, wherein the substrate is formed of a semiconductor material.

3. A micromachined filtering device according to claim 2, wherein the semiconductor material is silicon.

4. A micromachined filtering device according to claim 1, wherein the vias are arranged in an array.

5. A micromachined filtering device according to claim 4, wherein the first and second electrodes are interdigitized with respect to each other and with respect to the array of vias so that each via separates a portion of the first electrode from a portion of the second electrode.

6. A micromachined filtering device according to claim 1, further comprising a computer connected to the micromachined filter device for continuous monitoring of the output signal.

7. A micromachined filtering device according to claim 1, wherein the micromachined filtering device is coupled to a catheter through which a fluid entraining the material flows to and through the micromachined filtering device.

8. A micromachined filtering device according to claim 1, wherein the substrate is a first substrate of at least two substrates of the micromachined filtering device, and a second of the at least two substrates comprises a first surface, an oppositely-disposed second surface, a thickness defined by and between the first and second surfaces thereof, a plurality of vias through the thickness of the second substrate, and first and second electrodes on the first surface of the second substrate, the second substrate being fluidically downstream from the first substrate.

9. A micromachined filtering device according to claim 8, wherein the vias of the second substrate have approximately equal diameters that are smaller than the diameters of the vias of the first substrate so as to be capable of trapping a second material that passed through the vias of the first substrate, the second material collecting at the first surface of the second substrate.

10. A micromachined filtering device according to claim 9, wherein the first and second electrodes on the first surface of the second substrate are located so that the second material that collects at the first surface of the second substrate will electrically connect the first and second electrodes of the second substrate to produce a second output signal in proportion to the amount of the second material collected at the first surface of the second substrate.

11. A micromachined filtering device according to claim 8, wherein the second surface of the first substrate is bonded to the first surface of the second substrate, and the first and second substrates are enclosed in a housing.

12. A micromachined filtering device according to claim 8, wherein the first and second substrates are supported by first and second packages, respectively, the first and second packages being secured to each other.

13. A micromachined filtering device according to claim 1, the micromachined filtering device farther comprising means located fluidically upstream from the substrate for determining the density of a fluid subsequently flowed through the substrate.

14. A micromachined filtering device according to claim 1, the micromachined filtering device farther comprising means for sensing the pH of a fluid flowed through the micromachined filtering device.

15. A micromachined filtering device according to claim 1, the micromachined filtering device further comprising at least one chemical sensor for detecting at least one constituent of a fluid flowed through the micromachined filtering device, the at least one constituent being chosen from the group consisting of glucose, protein, urobilinogen, bilirubin, ketones, nitrite, pH, sodium, chlorine, potassium, magnesium, urea, uric acid, bicarbonate, sulfate, phosphate, and calcium.

16. A micromachined filtering device comprising at least two substrates in fluidic series, each of the substrates having a first surface, an oppositely-disposed second surface, a thickness defined by and between the first and second surfaces thereof, a plurality of vias through the thickness thereof, and first and second electrodes on the first surface thereof, wherein:

the vias of the first substrate are spaced apart and have approximately equal first diameters that prevent passage through the first substrate of a first material having a diametrical dimension greater than the first diameters and permit passage through the first substrate of a second material having a diametrical dimension less than the first diameters;

the first and second electrodes of the first substrate are located on the first surface thereof so that the first material that collects at the first surface of the first substrate will electrically connect the first and second electrodes of the first substrate to produce a first output signal in proportion to the amount of the first material collected at the first surface of the first substrate;

the vias of the second substrate are spaced apart and have approximately equal second diameters that are smaller than the first diameters of the first substrate and that prevent passage through the second substrate by the second material as a result of the second material having a diametrical dimension greater than the second diameters; and the first and second electrodes of the second substrate are located on the first surface thereof so that the second material that collects at the first surface of the second substrate will electrically connect the first and second electrodes of the second substrate to produce a second output signal in proportion to the amount of the second material collected at the first surface of the second substrate.

17. A micromachined filtering device according to claim 16, wherein the first and second substrates are formed of silicon.

18. A micromachined filtering device according to claim 16, wherein, for each of the first and second substrates, the vias thereof are arranged in an array, and the first and second electrodes thereof are interdigitized with respect to each other and with respect to the array of vias so that each via separates a portion of the first electrode from a portion of the second electrode.

19. A micromachined filtering device according to claim 16, further comprising a computer connected to the micromachined filter device for continuous monitoring of the first and second output signals.

20. A micromachined filtering device according to claim 16, wherein the micromachined filtering device is coupled to a catheter through which urine entraining the first and second materials flows to and through the micromachined filtering device.

21. A micromachined filtering device according to claim 16, wherein, for each of the first and second substrates, the second surface thereof has a recess formed therein to define a membrane surrounded by a frame, and the vias thereof extend through the membrane thereof, and wherein the frame of the first substrate is bonded to the frame of the second substrate and the first and second substrates are enclosed in a housing.

22. A micromachined filtering device according to claim 16, wherein the first and second substrates are supported by first and second packages, respectively, the first and second packages being secured to each other.

23. A micromachined filtering device according to claim 16, the micromachined filtering device further comprising means located fluidically upstream from the first substrate for determining the density of a fluid flowed through the micromachined filtering device.

24. A micromachined filtering device according to claim 16, the micromachined filtering device further comprising means for sensing the pH of a fluid flowed through the micromachined filtering device.

25. A micromachined filtering device according to claim 16, the micromachined filtering device further comprising at least one chemical sensor for detecting at least one constituent of a fluid flowed through the micromachined filtering device, the at least one constituent being chosen from the group consisting of glucose, protein, urobilinogen, bilirubin, ketones, nitrite, pH, sodium, chlorine, potassium, magnesium, urea, uric acid, bicarbonate, sulfate, phosphate, and calcium.

26. A method of filtering a fluid containing a first material having a first diametrical dimension and a second material having a second diametrical dimension that is less than the first diametrical dimension, the method comprising the steps of:

flowing the fluid through a micromachined filtering device that comprises a substrate having a first surface, an oppositely-disposed second surface, a thickness defined by and between the first and second surfaces, and a plurality of vias through the thickness of the substrate, the vias being spaced apart and having approximately equal diameters that permit passage through the substrate by the second material and that prevent passage through the substrate by the first material; and sensing the amount of the first material that collects at the first surface of the substrate with first and second electrodes located on the first surface so that the first material electrically connects the first and second electrodes to produce an output signal in proportion to the amount of the first material collected at the first surface.

27. A method according to claim 26, wherein the fluid is chosen from the group consisting of urine, blood, beverages, pharmaceutical mixtures, water, oils, fuels, and industrial chemicals.

28. A method according to claim 26, wherein the substrate is formed of silicon and the vias are defined in the silicon by etching.

29. A method according to claim 26, further comprising the step of continuously monitoring the output signal with a computer connected to the micromachined filtering device.

30. A method according to claim 26, further comprising the step of coupling the micromachined filtering device to a catheter through which the fluid flows to and through the micromachined filtering device.

31. A method according to claim 26, wherein the substrate is a first substrate of at least two substrates of the micromachined filtering device, the method further comprising the steps of:

after the fluid has flowed through the first substrate, flowing the fluid through a second of the at least two substrates, the second substrate having a first surface and an oppositely-disposed second surface, a thickness defined by and between the first and second surfaces, and a plurality of vias through the thickness of the second substrate, the vias being spaced apart and having approximately equal diameters that prevent passage through the second substrate by the second material; and sensing the amount of the second material that collects at the first surface of the second substrate with first and second electrodes located on the first surface so that the second material electrically connects the first and second electrodes to produce a second output signal in proportion to the amount of the second material collected at the first surface.

32. A method according to claim 31, further comprising the step of manufacturing the micromachined filtering device by bonding the second surface of the first substrate to the first surface of the second substrate and then enclosing the first and second substrates in a housing.

33. A method according to claim 31, further comprising the step of manufacturing the micromachined filtering device by supporting the first and second substrates with first and second packages, respectively, and then securing the first and second packages to each other.

34. A method according to claim 26, further comprising the step of, before the fluid has flowed through the substrate, flowing the fluid through means located fluidically upstream from the first substrate for determining the density of the fluid.

35. A method according to claim 26, the method further comprising the step of sensing the pH of the fluid as it flows through the micromachined filtering device.

36. A method according to claim 26, the method further comprising the step of detecting at least one constituent of the fluid as it flows through the micromachined filtering device, the at least one constituent being chosen from the group consisting of glucose, protein, urobilinogen, bilirubin, ketones, nitrite, pH sodium, chlorine, potassium, magnesium, urea, uric acid, bicarbonate, sulfate, phosphate, and calcium.

37. A method of filtering a fluid with a micromachined filtering device comprising at least two substrates in a fluidic series, the fluid containing a first material having a first diametrical dimension and a second material having a second diametrical dimension that is less than the first diametrical dimension, the method comprising the steps of:

flowing the fluid through vias in a first of the at least two substrates, the first substrate having a first surface, an oppositely-disposed second surface, and a thickness defined by and between the first and second surfaces, the vias extending through the thickness of the first substrate and having approximately equal diameters that permit passage through the first substrate by the second material and that prevent passage through the first substrate by the first material;

sensing the amount of the first material that collects at the first surface of the first substrate with first and second electrodes located on the first surface so that the first material electrically connects the first and second electrodes to produce a first output signal in proportion to the amount of the first material collected at the first surface;

after the fluid has flowed through the first substrate, flowing the fluid through vias in a second of the at least two substrates, the second substrate having a first surface, an oppositely-disposed second surface, and a thickness defined by and between the first and second surfaces, the vias extending through the thickness of the second substrate and having approximately equal diameters that prevent passage through the second substrate by the second material; and sensing the amount of the second material that collects at the first surface of the second substrate with first and second electrodes located on the first surface so that the second material electrically connects the first and second electrodes to produce a second output signal in proportion to the amount of the second material collected at the first surface.

38. A method according to claim 37, wherein the fluid is chosen from the group consisting of urine, blood, beverages, pharmaceutical mixtures, water, oils, fuels, and industrial chemicals.

39. A method according to claim 37, wherein the first and second substrates are formed of silicon and the vias thereof are defined in the silicon by etching.

40. A method according to claim 37, further comprising the step of continuously monitoring the first and second output signals with a computer connected to the micromachined filtering device.

41. A method according to claim 37, further comprising the step of coupling the micromachined filtering device to a catheter through which the fluid flows to and through the micromachined filtering device.

42. A method according to claim 37 wherein, for each of the first and second substrates, a recess is etched in the second surface thereof to define a membrane surrounded by a frame, and the vias thereof extend through the membrane thereof, the method further comprising the step of manufacturing the micromachined filtering device by bonding the frame of the first substrate to the frame of the second substrate and then enclosing the first and second substrates in a housing.

43. A method according to claim 37, further comprising the step of manufacturing the micromachined filtering device by supporting the first and second substrates with first and second packages, respectively, and then securing the first and second packages to each other.

44. A method according to claim 37, further comprising the step of, before the fluid has flowed through the first substrate, flowing the fluid through means located fluidically upstream from the first substrate for determining the density of the fluid.

45. A method according to claim 37, the method further comprising the step of sensing the pH of the fluid as it flows through the micromachined filtering device.

46. A method according to claim 37, the method further comprising the step of detecting at least one constituent of the fluid as it flows through the micromachined filtering device, the at least one constituent being chosen from the group consisting of glucose, protein, urobilinogen, bilirubin, ketones, nitrite, pH, sodium, chlorine, potassium, magnesium, urea, uric acid, bicarbonate, sulfate, phosphate, and calcium.

* * * * *